United States Patent [19]

Cumins et al.

[11] Patent Number: 4,905,678
[45] Date of Patent: Mar. 6, 1990

[54] HIP STABILIZER

[75] Inventors: David L. Cumins, Rio Vista; Larry T. Randolph, Arlington, both of Tex.

[73] Assignee: Medical Designs, Inc., Azale, Tex.

[21] Appl. No.: 259,164

[22] Filed: Oct. 18, 1988

[51] Int. Cl.⁴ .............................................. A61F 5/02
[52] U.S. Cl. .................................... 128/78; 188/80 R
[58] Field of Search ........................... 128/78, 80 R, 68

[56] References Cited

U.S. PATENT DOCUMENTS

| | | | |
|---|---|---|---|
| 552,143 | 12/1895 | Rankin | 128/88 |
| 649,237 | 5/1900 | Dyson | 128/88 |
| 2,332,119 | 10/1943 | Springer | 128/78 |
| 2,778,358 | 1/1957 | Keles | 128/78 |
| 4,173,973 | 11/1979 | Hendricks | 128/78 |
| 4,481,941 | 11/1984 | Rolfes | 128/88 |
| 4,522,199 | 6/1985 | Waddell et al. | 128/80 G |
| 4,556,053 | 12/1985 | Irons | 128/88 |
| 4,715,364 | 12/1987 | Naguchi | 128/78 |

FOREIGN PATENT DOCUMENTS

| | | | |
|---|---|---|---|
| 1324883 | 3/1963 | France | 128/80 F |
| 05625 | of 1911 | United Kingdom | 128/78 |

Primary Examiner—Edgar S. Burr
Assistant Examiner—Huong Q. Pham
Attorney, Agent, or Firm—James C. Fails; Arthur F. Zobal; Geoffrey A. Mantooth

[57] ABSTRACT

A hip stabilizer for a patient who still has control of the muscles in his leg to prevent atrophy of the muscles, characterized by a non-inflatable, adjustable belt, serving to engage the hips, the belt being adjustable for fitting the hips of any patient; a hip pad disposed on a desired side of the patient when in place, at least one metal biasing means on one of the hip pads for controlling the thigh of the patient at a desired angle of abduction in the range of from 0-90 degrees, preferably 0-15 degrees, with respect to the downwardly extending hip pad; non-inflatable, adjustable thigh engaging mechanism. In the preferred embodiment, the thigh engaging means includes a longitudinally extending member, a deformable plastic pad and a plurality of straps that extend around the pad and the thigh. It is also preferred that suitable padded material be interspersed, or disposed between the respective elements and the body. A pivotal interconnecting means allows the member of the thigh mechanism to be connected pivotally with the belt around the patient. Preferably the interconnecting means includes a means for limiting the degrees of flexion and extension allowed. Suitable details of construction for allowing adjusting of the elements as well as holding in place the buckle are disclosed.

5 Claims, 4 Drawing Sheets

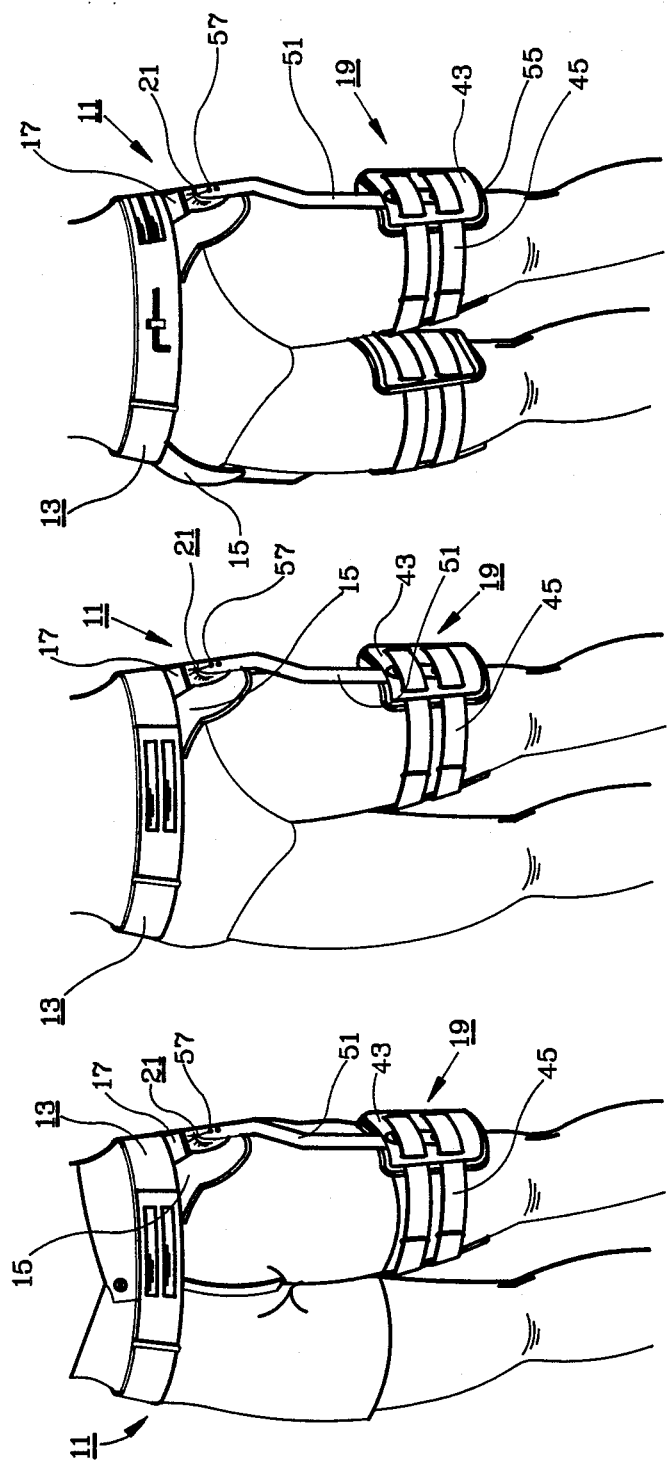

HIP STABILIZER

FIELD OF THE INVENTION

This invention relates to orthopedic hip braces. More particularly, this invention relates to braces for stabilizing a hip joint, while allowing limited movement of the thigh by the patient.

DESCRIPTION OF THE PRIOR ART

Typically, a patient suffering from a hip injury was placed into a cast which stabilized the hip joint but presented other problems. Such casts were frequently bulky, heavy and cumbersome. The patient was fixed in a rigid position which made handling and transportation difficult, if not impossible. To keep the patient from being bedridden and to make possible bathing and the like, inventions such as this invention were conceived and brought to fruition. These type hip stabilizers obviated the serious discomfort caused by casts and the like.

Moreover, these hip stabilizers obviated the problem of atrophy of the muscles and the deterioration of joints caused by complete immobilization of muscles and joints while a hip or related injury was healing.

A search of the prior art reveals a wide variety of approaches to braces ranging from the fracture apparatus of U.S. Pat. No. 9,483, showing a caliper at the knee, U.S. Pat. No. 2,092, showing the flexure of the fracture apparatus with the hinge at the knee through the following patents: 874,446; 1,043,648; 1,490,265; 1,939,097; 2,111,018; 2,332,119; 2,753,864; 2,778,358; 3,993,056; 4,169,467; 4,481,941. This last patent is one of the most pertinent ones found in this art and is described in the enclosed Patentability Brief.

Another pertinent patent is U.S. Pat. No. 4,531,515 showing the adjustable hinge brace for limiting movement and U.S. Pat. No. 4,602,627 showing the cable control ortho leg brace that has the elements strung on a cable. The elements in that patent apparatus are removable and the cable allows control without chafing. There are several foreign patents that are pertinent to this invention; including the following: U.K. No. 2,156,226; French No. 1,324,883; two German patent Nos. 71,093 and 405,399; Italian No. 340,681 and a couple of Russian patents, Nos. 925,341 and 1,204,209.

There is also an article entitled Bracing and Cerebral Palsy, American Academy, of Orthopedic Surgeons on General Bone and Joint Surgery, Volume 44A, No. 7, October, 1962, page 1457-1476.

The hip stabilization devices of the prior art regardless of whether they be called fracture apparatus, braces for palsy victim or the like, fail to provide respective hip pads on either side or on both sides with at least a semi-rigid belt and a biasing means for biasing in abduction as desired up to 90 degrees, preferably about 15 degrees in normal cases, even though they might have other desirable attributes.

SUMMARY OF THE INVENTION

Accordingly, it is an object of this invention to provide at least a semi-rigid belt and at least one respective hip pad adapted for either side or for both sides with biasing means for biasing in abduction, as desired up to 90 degrees, preferably up to about 15 degrees, as well as providing other desirable features as noted.

It is a specific object of this invention to provide a hip stabilization device with braces, hip pads, at least a semi-rigid belt and interchangeable members for providing a biasing force in abduction at angles up to 90 degrees, preferably about 15 degrees, providing adjustable thigh pads for adjusting to the length of the thigh of the wearer and providing a desired degree of control over the flexion allowed the patient.

These and other objects will become apparent from the descriptive matter hereinafter, particularly when taken into conjunction with the appended drawings.

In accordance with this invention there is provided a device for stabilizing the hip of a patient who has control of the muscles in his leg to enable the patient to voluntarily move his leg within a limited range characterized by non-inflatable, adjustable hip engaging means for adjustably engaging the patient's hips, or upper pelvic girdle; the hip engaging means comprising at least a semi-rigid band, or belt, that extends circumferentially at least more than half way around and past the opposing hip for a counter force; at least one hip pad, disposed on a desired hip on at least one side of the wearer and connected with a hip engaging means and extending below the hip engaging means so as to apply pressure to the hip of the patient when the hip engaging means is emplaced on the patient and a biasing means applies pressure to the given thigh; metallic biasing means for biasing in abduction, the thigh of the patient at a desired angle within the range of 0 to 90 degrees, preferably, 0 to 15 degrees in a normal case, with respect to the downwardly extending hip pad adjacent where the metal biasing means is placed; the metal biasing means being removably connected with the hip engaging means such that either hip of the patient can be connected with its respective thigh by the device at a desired angle of abduction maintained for either hip or thigh, singly or doubly; a non-inflatable adjustable thigh engaging means for adjustably engaging the patient's thigh; and a pivotally interconnecting means for pivotally interconnecting the metal biasing means and the member of the thigh engaging means for allowing pivotal movement thereof.

The metal biasing means is removably connected with the hip engaging means such that either hip of the patient can be connected with its respective thigh engaging means and a desired angle, or degree, of abduction maintained for either hip or thigh, singly or doubly. The thigh engaging means preferably includes a longitudinally extending member and a pad that is slidable therealong and can be fastened in any desired attained position, as well as a plurality of inelastic straps that are connected with a pad and adapted to encircle the thigh and the pad to force the pad into conforming engagement with the thigh.

BRIEF DESCRIPTION OF THE DRAWINGS

FIG. 1 is an isometric view, from a slight angle on the left side showing a single hip stabilizer in place on a patient's leg and hip.

FIG. 2 is an isometric view similar to that of FIG. 1 but showing how the hip stabilizer with its thigh engaging means can engage a bare leg if it is desired to wear it under clothing or the like.

FIG. 3 illustrates an isometric view of a hip stabilizer with two thigh engaging means in place.

DESCRIPTION OF THE PREFERRED EMBODIMENTS

Figure 4:
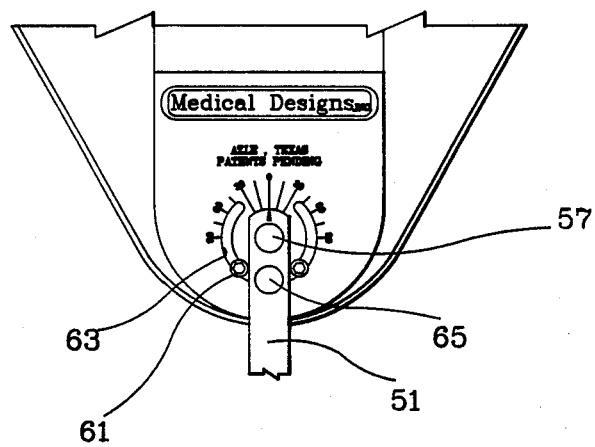
FIG. 4 is an isometric view from the front of the means for limiting the degree of pivotal movement, or limiting flexion.

This invention enables post operative hip management. In the illustrated embodiment, it maintains a leg in a desired degree of abduction and provides total flexion-extension control.

Referring to FIGS. 1–3, the hip stabilization device 11 is shown in place on a wearer. The hip stabilizer device 11 includes a hip engaging means 13, at least one hip pad 15, FIG. 1, a metallic biasing means 17, a thigh engaging means 19, and a pivotally interconnecting means 21.

Figure 5:
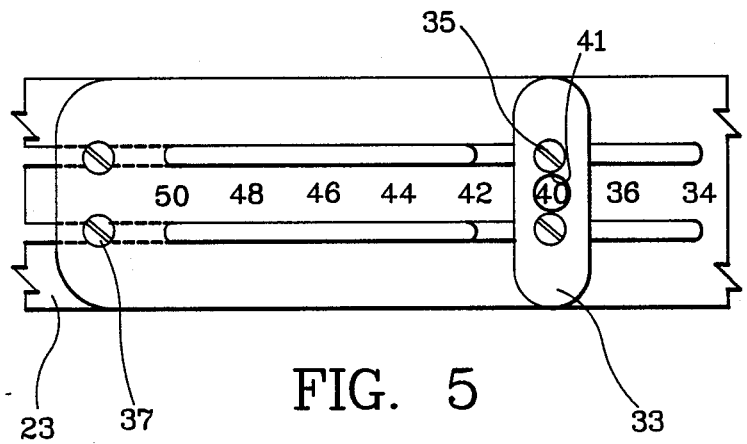
FIG. 5 is a frontal view of the adjustment for adjusting the length of the hip engaging means to fit a particular size hip.
Figure 6:
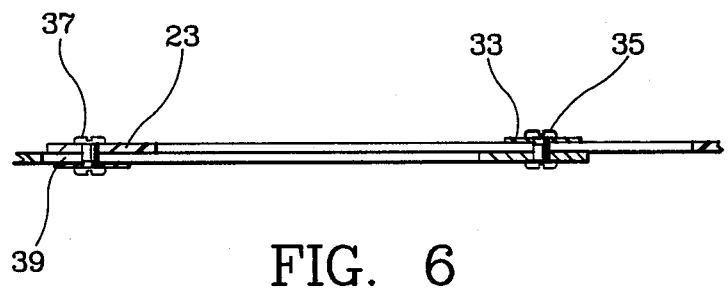
FIG. 6 is a partial cross-sectional view of the embodiment of FIG. 5.
Figure 7:
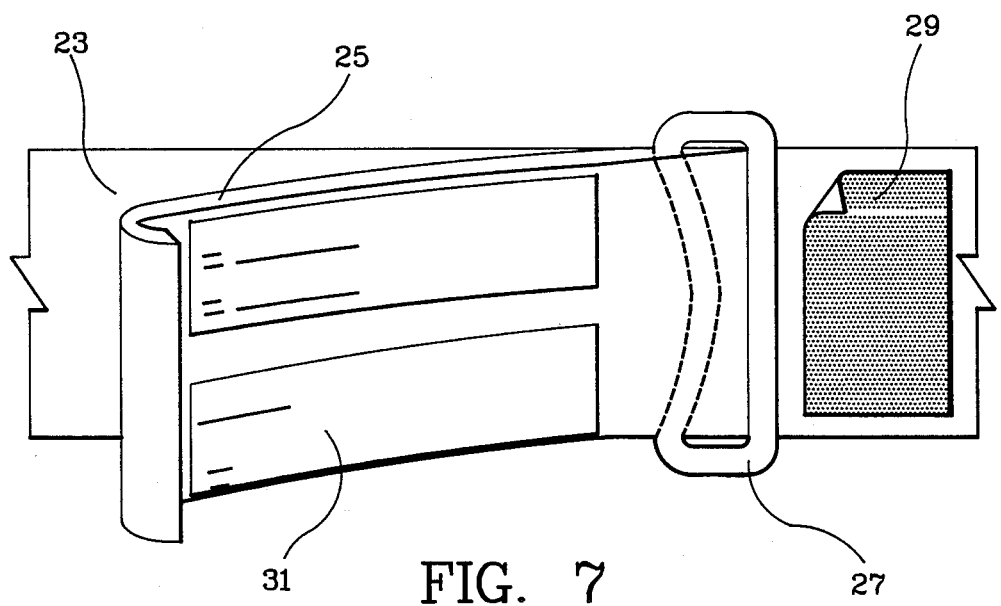
FIG. 7 is a partial isometric view of the hip engaging means with a buckle means and closely attached Velcro strips for holding the buckle means in place to prevent shifting.

The hip engaging means 13 comprises an at least rigid belt 23, FIGS. 5–7. The belt 23 should be at least semi-rigid enough to sustain a reaction force, or counter force, to a biasing force. For example, belt 23 may be a ⅛ inch thick by 3 ½ inch wide belt of leather, or heavy plastic. The belt 23 should extend circumferentially at least more than half way around the wearer so as to extend past the opposing hip for the counter force. The belt 23 has an interior side lined with foam padding 25 and an exterior side lined with foam padding. The foam padding may be of synthetic plastic such as polyurethane foam, polystyrene foam or the like. The belt 23 may be composed of leather or preferably a relatively only mildly flexible plastic so as to afford the desired rigidity. The belt 23 has a buckle means 27, FIG. 7 that is held in place intermediate a patch of VELCRO, a trademark for a fabric employing J-hooks and loops to fasten, 29 and doubled back foam padding and VELCRO strips 31. The other end of the belt 23 can be brought through the buckle means 27, bent back on itself and fastened by suitable VELCRO strips, also. The buckle means 27 is preferably a D-ring type buckle means through which the respective ends of the hip engaging means, such as padding, are passed and folded back upon the other padding and fastened with suitable Velcro tabs or the like. It is only necessary to fasten the hip engaging means with the foam padding 25, since the belt is not easily adapted to passing through the buckle means 27 and folding back on itself because of its relative inflexibility.

The belt 23 can be adjusted in size by sliding of suitable adjusting means illustrated by the fastener 33, FIG. 5. The fastener 33 has extending through it and through a plurality of slots, relatively co-engaging screwbolts 35. As is recognized, screwbolts have screw heads with threaded co-engaging shafts. Similarly, at the free end 36 of one-half of the belt there are screwbolts 37 that pass through respective slots 39 for adjusting in size and being fastened when the desired size is attained. As can be seen in the window 41 of the fastener 33, the size in inches can be shown. As illustrated, a 40 inch hip region is shown. This allows adjusting the relatively less flexible belt 23 to the size hips of the person wearing the hip engaging means and enables and facilitates fastening only with the foam padding and the buckle means 27.

Of course modifications of the hip engaging means can be employed, similar to those described in the prior art. In this invention it is relatively important that the hip engaging means have an at least semi-rigid band, or belt, that extends at least past the wearer's other hip for fastening the metal biasing means, as noted hereinbefore.

Each hip pad 15 includes both the stiff plastic material like the belt and the foam padding, such as synthetic plastic foam or the like for cushioning the hips adjacent the patient and prevents chafing, discomfort and the like. While there is always at least one hip pad disposed on a desired hip on at least one side of the wearer, a pair of hip pads may be employed for both hips of the wearer if desired, similarly as illustrated in FIG. 3. The hip pads can be formed integrally with the belt and the foam padding of the hip engaging means if desired. They underlie the metal biasing means and prevent any discomfort caused by the metallic biasing means 17.

Figure 9:
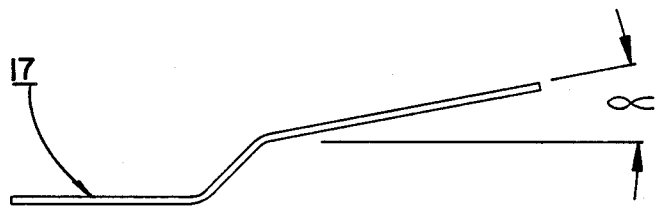
FIG. 9 is a partial isometric view of a metallic biasing bolted by screws to the hip engaging means, with the outer foam padding stripped away.

The metallic biasing means 17 are formed of a relatively unbending piece of metal for biasing the thigh of the patient at a desired angle within the range of 0 to 90 degrees, preferably, for most cases in the range of 0 to 15 degrees, in abduction with respect to downwardly extending hip pad. The metallic biasing means 17 is bent at an angle, FIG. 9, for biasing the thigh in abduction, when that feature is employed. While the angle may go up to as high as 90 degrees in the case of certain very young patients, it ordinarily will be in the range of 0 to 15 degrees in most cases. The metallic biasing means are connected, as by screws, bolts or the like through apertures in the belt 23 such that either hip of the patient can be connected with its respective thigh by the hip stabilization device at a desired angle of abduction maintained at the desired angle. There are provided respective sets of apertures for insertion therethrough of the screws or the like on both sides of the belt 23. In this way, the metallic biasing means 17 can be emplaced on either the right or the left or both hips of the patient. Since the metallic member must be bent to the desired degree of biasing in abduction, however, it is necessary to specify the angle of abduction before the metallic biasing means is bent and fastened to the hip engaging means, as through three apertures, and connected with bolts, screwbolts or the like, so as to hold the thigh engaging means 19.

Figure 8:
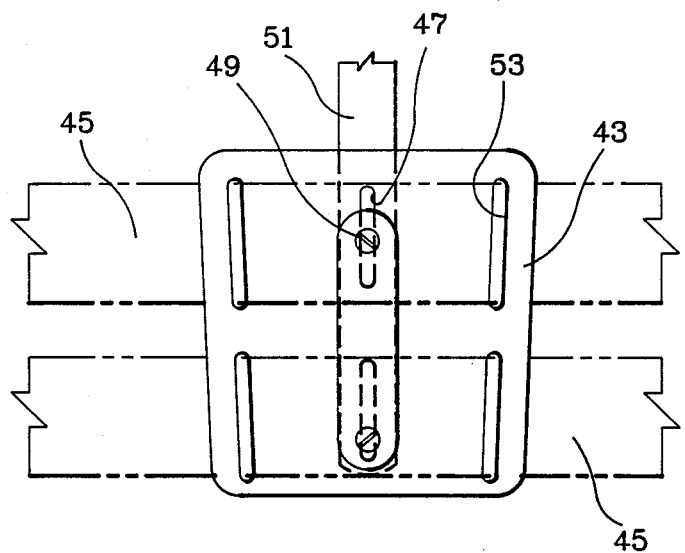
FIG. 8 is a front elevational view of the thigh engaging pad and the means for adjusting the length of the thigh engaging means to secure proper placement of the pad on the thigh of the patient.

The thigh engaging means 19 comprises an arcuate shaped plastic support, or shield 43, FIG. 8, which is shaped to conform to the natural curvature of the thigh when encircled and pulled into conforming fit by the respective straps 45. The plastic support 43 is in the nature of a deformable but semi-rigid plastic, such as a thermoplastic like PVC (polyvinyl chloride), ABS (acrylonitrile butadiene styrene copolymer), polypropylene, polycarbonate or other thermoplastic material.

The plastic support 43, has a plurality of slots 47 and co-engaging screwbolts 49 that enable the screws to be loosened and slid longitudinally of the brace 51 to be able to adjust to the length of the thigh. Additional slots 53 receive straps for encircling the thigh engaging means, or plastic support 43, as shown by the ghost lines in FIG. 8, and pulling it into conforming shape. How the support 43 is pulled into conforming engagement with the foam padding 55 in place can be seen in FIGS. 1-3. As illustrated, there are a plurality of at least two straps 45 that are relatively inelastic for pulling the thigh engaging means 19 into conforming fit with the thigh after the length has been adjusted to the right length to fit the thigh. If desired, of course, a single strap or more than two straps could be employed. A foam pad 55, FIG. 3, prevents discomfort from a contact of the thigh of the patient with the relatively less comfortable material such as the brace 51 or the plastic support 43. If desired, an additional plate and padding may be employed in the inside of the leg, or other side as illustrated in FIGS. 1-3.

Figure 10:
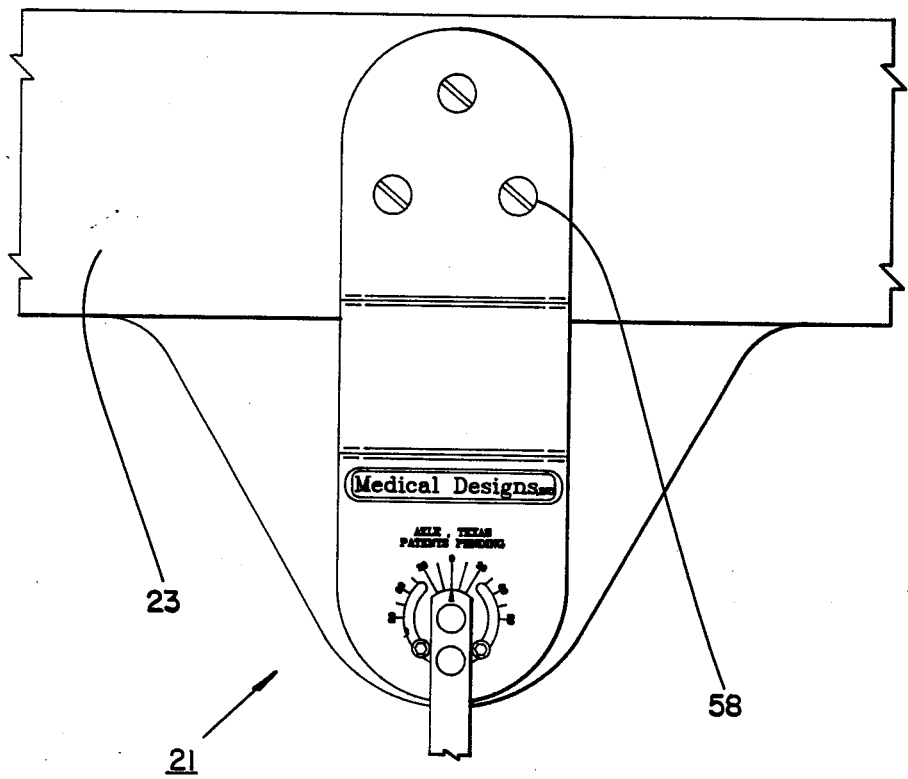
FIG. 10 is a front elevational view of the belt, or at least semi-rigid band, and with a limiting type hinge means at its lower end.

As illustrated, the interconnecting means 21 includes a hinge in which the brace 51 is hingedly mounted about a pivot shaft 57. As illustrated, the pivot shaft 57 is a bradded shaft that cannot be replaced. If desired, however, the bradded shaft could be a suitable screwbolt or the like that could be replaced. The interconnecting means 21, is fastened to the belt 23 by a plurality of screwbolts 58, FIG. 10.

In the illustrated preferred embodiment, a second bradded bolt 65, FIG. 4, extends through the member 61 and traverses along the arcuate slot 63. The arcuate slot 63 also contains a plurality; such as at least two Allen head bolts that can be positioned to limit the degrees of flexion or extension allowed to the patient's thigh. The second bradded pin shaft 67 aids in maintaining better control of the member 51. The member 51, or brace 51, is preferably of metallic or other material that will sustain the stress introduced by the metallic biasing means without deforming, or cold flowing, under the continued stress.

In operation, the device can be applied to either side of the hips. The belt 23 with its metallic biasing means in place for either the right or left hip or both is fit to the hips, or upper hip region, of the patient. Alignment is achieved with the thigh and the hip and the length of the thigh engaging means is adjusted so that the thigh engaging means can be emplaced after the hip engaging means is adjusted to fit the hips.

The straps 45 are passed around the thigh and thigh engaging means including the plastic support 43 to fit the thigh and thigh engaging means together. In this way the patient still has control of the muscles so atrophy is minimized, yet the hip is stabilized for healing. The desired degree of abduction is achieved and maintained by the metal biasing means. The flexion and extension is controlled by movement of the respective Allen head screws 61 around the arcuate slot 63 to respective desired positions.

If desired, the device can be quickly detached as for hygiene or the like.

The components can be stored in a disassembled form and take up much less space than in the connected form. The device can be re-used on a patient with an injury on either or both hips as desired. Moreover, the position of the Allen head bolts 61 can be changed a desired degrees of flexion and extension change so that the hip stabilizer has substantially universal applicability.

Although this invention has been described with a certain degree of particularity, it is understood that the present disclosure is made only by way of example and that numerous changes in the details of construction and the combination and arrangement of parts may be resorted to without departing from the spirit and the scope of the invention, reference being had for the latter purpose to the appended claims.

What is claimed is:

1. A device for stabilizing the hip of a patient who has control of the muscles in his leg to enable the patient to voluntarily move his leg only within a control range as desired, comprising:
   a. non-inflatable, adjustable hip engaging means for adjustably engaging a patient's hips; said hip engaging means comprising at least a semi-rigid band that extends circumferentially at least more than half way around the wearer and past the opposing hip to provide a counter force;
   b. means to apply pressure to a respective hip of a patient when said hip engaging means is emplaced on the patient and the patient's thigh is moved in abduction or addiction including at least one hip pad disposed adjacent a desired hip on at least one side of the wearer and connected with said hip engaging means and extending well below said hip engaging means and
   c. at least one metallic biasing means for biasing in abduction the thigh of the patient at a desired angle up to 90 degrees with respect to the downwardly extending hip pad adjacent to where said metal biasing means is placed; said metallic biasing means including a member that is metal and bendable to a desired angle and rigid enough to bias in abduction once bent to a desired angle and being employed adjacent each said hip pad;
   d. non-inflatable, adjustable thigh engaging means for adjustably engaging the patient's thigh; said non-inflatable thigh engaging means comprising:
      i. a longitudinally extending member connected with said metallic biasing means;
      ii. a support pad, connected with said member and adapted for fitting the patient's thigh; iii. at least one strap connected with said pad and adapted to encircle the thigh of the patient and said support pad and hold said support pad in conforming engagement with said thigh; and
   e. pivotally interconnecting means for pivotally interconnecting said metallic biasing means and said member of said thigh engaging means for controlling the range of flexion and extension.

2. The device of claim 1 wherein said hip engaging means has slots and includes at least two overlapping sectors with respect to said slots and wherein a fastener extends through said slots for fastening said sectors to each other once a desired length of said hip engaging means is attained for fitting a particular patient.

3. The device of claim 1 wherein there are provided a pair of hip pads, one on each hip on each side of the wearer.

4. The device of claim 3 wherein there are provided a pair of metallic biasing means, one adjacent each of said hip pads.

5. The device of claim 1 wherein said hip engaging means has a modified d-ring type buckle means through which one end of said hip engaging means extends, wherein a VELCRO fastener is adjacent said buckle means for holding said buckle means in place and wherein the other end of said hip engaging means is adapted to be passed through said buckle means and has VELCRO tabs for being reconnected to itself after it has been folded back adjacent itself.

* * * * *

UNITED STATES PATENT AND TRADEMARK OFFICE
CERTIFICATE OF CORRECTION

PATENT NO. : 4,905,678

DATED : March 6, 1990

INVENTOR(S) : David L. Cumins, et al

It is certified that error appears in the above—identified patent and that said Letters Patent is hereby corrected as shown below:

On the title page:

In the assignee's address; please correct the spelling of the town from "Azale" to --Azle--.

Column 6, line 18, please delete "addiction" and substitute therefor --adduction--.

Column 6, line 38, element iii, please make it a separate sub-paragraph.

Signed and Sealed this

Twenty-sixth Day of February, 1991

Attest:

HARRY F. MANBECK, JR.

*Attesting Officer*     *Commissioner of Patents and Trademarks*